United States Patent [19]

Sage, Jr. et al.

[11] Patent Number: 5,334,138
[45] Date of Patent: Aug. 2, 1994

[54] METHOD AND COMPOSITION FOR INCREASED SKIN CONCENTRATION OF ACTIVE AGENTS BY IONTOPHORESIS

[75] Inventors: Burton H. Sage, Jr.; Jim E. Riviere, both of Raleigh, N.C.

[73] Assignees: North Carolina State University, Raleigh, N.C.; Becton Dickinson and Company, Franklin Lakes, N.J.

[21] Appl. No.: 653,204

[22] Filed: Feb. 8, 1991

Related U.S. Application Data

[63] Continuation-in-part of Ser. No. 494,062, Mar. 15, 1990, abandoned.

[51] Int. Cl.$^5$ ............................................. A61N 1/30
[52] U.S. Cl. ........................................ 604/20; 604/49; 128/898
[58] Field of Search ............... 604/20; 128/798, 802, 128/803

[56] References Cited

U.S. PATENT DOCUMENTS

| | | | |
|---|---|---|---|
| 3,991,755 | 11/1976 | Vernon et al. | 604/20 |
| 4,474,570 | 10/1984 | Ariura et al. | 604/20 |
| 4,702,732 | 10/1987 | Powers et al. | 604/20 |
| 4,752,285 | 6/1988 | Petelenz et al. | 604/20 |
| 4,845,233 | 7/1989 | Higuchi | 548/320 |
| 5,023,085 | 6/1991 | Francoeur et al. | 604/20 |
| 5,047,007 | 9/1991 | McNichols et al. | 604/20 |
| 5,057,072 | 10/1991 | Phipps | 604/20 |
| 5,068,226 | 11/1991 | Weinshenker et al. | 604/20 |
| 5,084,006 | 1/1992 | Lew et al. | 604/20 |
| 5,084,008 | 1/1992 | Phipps | 604/20 |
| 5,087,620 | 2/1992 | Parab | 574/171 |
| 5,135,480 | 8/1992 | Bannon et al. | 604/20 |

OTHER PUBLICATIONS

Lattin, Gary A. "Method to Control Delivery of Uncharged Drugs Via Iontophoresis" JRE Nov. 1988.
J. L. Bezzant et al., "Journal of the American Academy of Dermatology" 19:869 (1988).
L. P. Gangarosa, Method and Find Exptl. Clin Pharmacol 3:83 (1981).
K. G. Dhuner, Acta Anaesthesiol. Scand, (1972). Mepivacaine and Vasoconstrictors in Regional Anaesthesia.
L. P. Ganagarosa et al. Journal of Pharmaceutical Sciences, 67, 1439-1443 (1978).

Primary Examiner—C. Fred Rosenbaum
Assistant Examiner—Michael Rafa
Attorney, Agent, or Firm—Bell Seltzer Park & Gibson

[57] ABSTRACT

The invention discloses methods and compositions for enhanced skin concentration of iontophoretic delivered active agents. The compositions are pharmaceutically acceptable compositions for iontophoretic delivery which comprise a skin concentration enhancing amount of a vasoconstrictor and active agent. Methods comprise adding a skin concentration enhancing amount of a vasoconstrictor to an active agent and delivering by iontophoresis.

14 Claims, 5 Drawing Sheets

METHOD AND COMPOSITION FOR INCREASED SKIN CONCENTRATION OF ACTIVE AGENTS BY IONTOPHORESIS

CROSS-REFERENCE TO ELATED APPLICATION

This application is a continuation-in-part of patent application Ser. No. 07/494,062, filed Mar. 15, 1990 abandoned.

FIELD OF THE INVENTION

The invention relates to iontophoretic transdermal delivery. More specifically, the invention relates to methods and compositions for enhancing skin concentration of iontophoretic delivered active agents.

BACKGROUND

During iontophoresis, charged compounds pass from a reservoir attached to the skin of a person or animal into the tissue therebeneath. The process is one wherein the rate of delivery is a function of current, active agent concentration, and presence of other ions. It is a generally held belief that higher concentration of compound, higher levels of current, and lower concentration of other ions will result in greater delivery of the compound.

L. Brown and R. Langer, *Ann. Rev. Med.* 39:221 (1988) describe the generally held belief that the rate limiting barrier for transdermal drug delivery is the stratum corneum. There continues to be a large research effort to find methods to reduce or eliminate the rate limiting property of the stratum corneum.

N. H. Bellantone et al., *International Journal of Pharmaceutics* 30:63 (1986) describes how iontophoresis can be used in place of other means to enhance drug transport through the epidermal barrier such that the need for chemical penetration enhancers could be obviated. Alternatively, the article suggests use of penetration enhancers could lower drug concentrations or lower energy required for delivery.

Another technique believed to enhance the delivery of certain types of active agents by iontophoresis is disclosed in European patent application 0 278 473 A1. The application describes the addition of compounds to proteins and other macromolecules to decrease the degree of aggregation of the molecules in the active reservoir. The added compounds have the ability to aid solubility and disassociation of the macromolecules.

It is also well-known in the iontophoresis art (for example, see "Iontophoretic Delivery of Nonpeptide Drugs 'Formulation Optimum for Maximum Skin Permeability'" by J. E. Sanderson et al, *J. Pharm Sci.* 78:361 (1989) that the presence of ions other than the desired compound in the donor reservoir formulation reduces iontophoretic efficiency.

In the situation of transdermal delivery where the rate limiting barrier is the stratum corneum, the dermal vasculature, which acts as the means of compound removal from the dermal tissue, has no effect on the delivery rate. Regardless of its state of dilation, it is capable of removing all the compound that reaches it. Otherwise, the vasculature would become the rate limiting barrier.

However, when the stratum corneum is not a rate limiting barrier, the vasculature is more important. It would be desirable to obtain compositions and methods for iontophoretic delivery that are directed toward utilizing the vasculature.

SUMMARY OF THE INVENTION

The invention discloses methods and compositions for enhanced skin concentrations of iontophoretic delivered active agents.

The compositions are pharmaceutically acceptable compositions for iontophoretic delivery comprising an enhancing skin concentration amount of a vasoconstrictor and active agent.

Other embodiments of the invention include methods for enhancing the skin concentration of iontophoretic delivered active agents comprising adding a skin concentration enhancing amount of a vasoconstrictor to an active agent and delivering by iontophoresis.

DETAILED DESCRIPTION OF THE INVENTION

Figure 1:
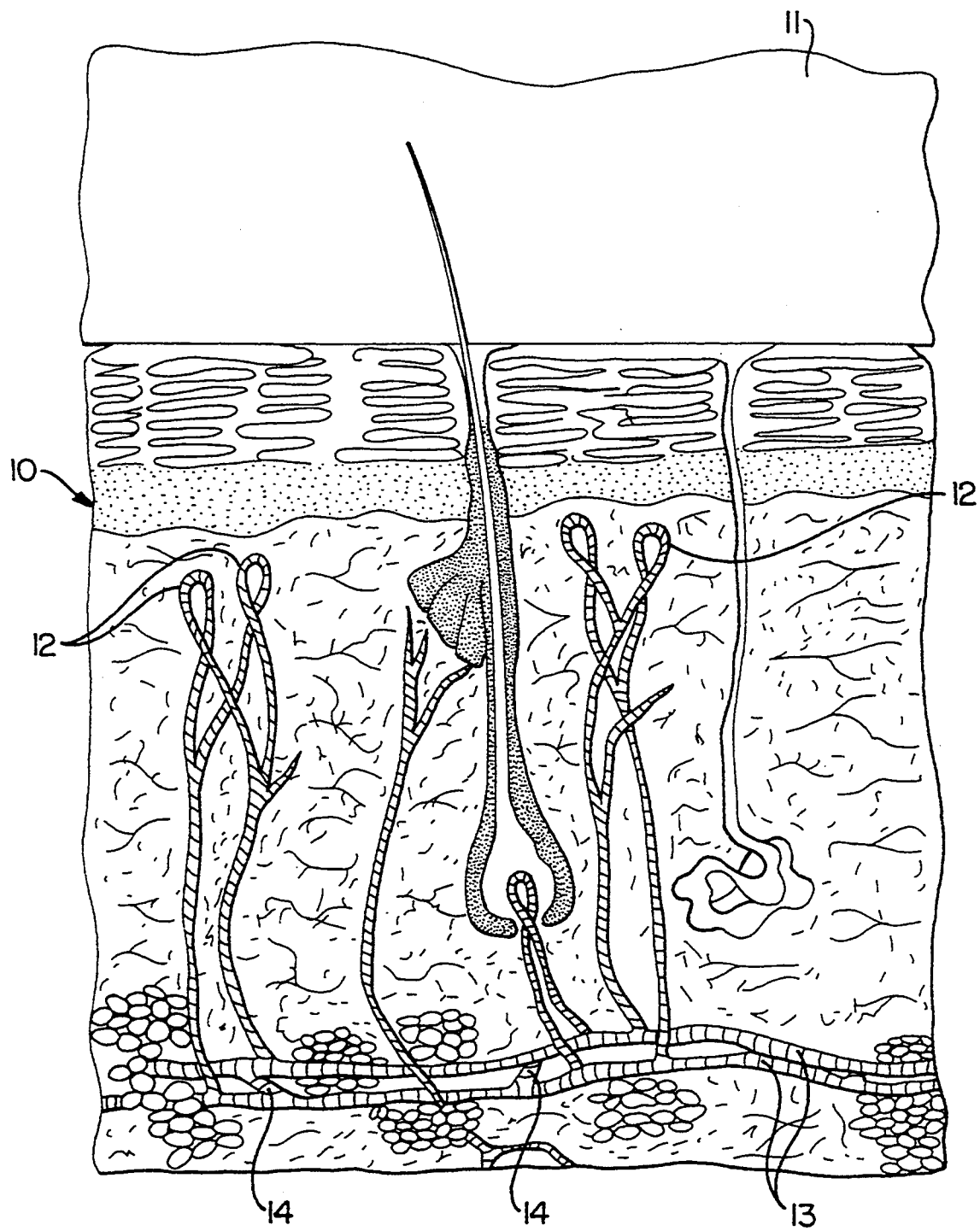
FIG. 1 A schematic presentation of the skin (10), which shows the upper capillary loops (12) of the vasculature of the skin and the deeper blood vessels that feed the upper capillary loops and the shunt blood vessels (14) which connect the deeper blood vessels.

While this invention is satisfied by embodiments in many different forms, there is shown in the drawings and will herein be described in detail, preferred embodiments of the invention, with the understanding that the present disclosure is to be considered as exemplary of the principles of the invention and is not intended to limit the invention to the embodiments illustrated. The scope of the invention will be measured by the appended claims and their equivalents.

The present invention discloses methods and compositions for enhancing skin concentrations of iontophoretic delivered active agents.

Embodiments of the invention include pharmaceutically acceptable compositions for iontophoretic delivery comprising a skin concentration enhancing amount of vasoconstrictor and active agent.

In addition, embodiments of the invention provide methods for enhancing skin concentration of iontophoretic delivered active agents comprising:
  (a) adding a skin concentration enhancing amount of a vasoconstrictor to an active agent; and
  (b) delivering a pharmaceutically acceptable composition of (a) by iontophoresis.

The methods and compositions of the present invention are particularly advantageous compared to prior methods and compositions. Prior methods and compositions typically relied on skin damaging or skin altering compositions such as permeation enhancers. Unlike skin permeation enhancers that alter the stratum corneum, the compositions and methods of the present invention are not directed toward altering the stratum corneum and yet achieve an enhanced skin concentration with iontophoretic delivered active agents. Likewise, the benefits obtained by the addition of a vasoconstrictor to an active agent is opposite the generally held belief that lower concentration of other ions is necessary for delivery.

The following terms are defined as used in this document. "Ion" refers to an atom or radical that has lost or gained one or more electrons to acquire an electric charge. "Active agent" refers to the entity chosen to be delivered by iontophoresis. Thus, active agent refers to the chosen entity and the ionic form of the chosen entity for delivery, such as halide salts of a chosen entity to be delivered (e.g., lidocaine and an ionic form of lidocaine for delivery such as lidocaine hydrochloride). "Patient" refers to animals, including humans, household animals such as dogs and cats, livestock such as cattle, horses, sheep, pigs, goats and rabbits, laboratory animals such as mice and rats, and zoo animals such as exotic species.

The methods and compositions of the invention are not limited to practice with any one particular iontophoretic system. Generally, iontophoretic devices comprise at least two electrodes, an electrical energy source (e.g., a battery) and at least one reservoir which contains an active agent to be delivered. Several iontophoretic devices are known, such as those disclosed in P. Tyle, *Pharmaceutical Biosearch* 3:318 (1986).

Key components of the skin, as shown in FIG. 1, are the stratum corneum, epidermis, dermis and more specifically, the blood vessels of the dermis. In systemic drug delivery, the objective is to get the drug from a donor reservoir adjacent to the stratum corneum into the blood stream. In topical drug delivery, the objective is to get the drug from the donor reservoir adjacent to the stratum corneum into the skin below the stratum corneum while avoiding removal by the blood stream. Therefore, the structure of both the stratum corneum and the vascular is important.

When iontophoresis of an active agent is performed, the compound passes through the stratum corneum, through the intervening dermal tissue and into the vasculature. In a situation wherein the stratum corneum is the rate-limiting barrier, the blood flow in the vasculature is of little consequence. When the rate of delivery of the active agent is enhanced over passive delivery, as in the case of iontophoresis, to the point where the ability of the vasculature to remove the compound is rate limiting, then the blood flow in the vasculature becomes significant. Iontophoresis of a vasoconstrictor with an active agent, therefore, is believed to constrict blood flow, thus enhancing the skin concentration of iontophoretic delivered active agents.

The ability to maintain proper concentration ratios of active agent to vasoconstrictor will depend upon the iontophoretic properties of the active agent and vasoconstrictor, and hence the relative proportions of the vasoconstrictor combined with the active agent.

It is understood that most active agents have more than one effect in the body. For example, lidocaine is a local anesthetic which also exhibits vasoactive properties (i.e. a vasolidator). Therefore, consideration of these factors for any active agent must be taken into account when determining optimum ranges of each for iontophoretic delivery together.

The response surface method (RSM) is a known method that can be used to study the effects of active agent properties and vasoconstrictor properties. Other methods for measuring the effects of the active agent and vasoconstrictor are known. Other methods can be found in Chapter II of P. D. Halland, Experimental Design In Biotechnology (Marcell Dekker Inc., (1989) N.Y.).

The response surface method can be used to determine the optimum concentrations of a composition of the active agent lidocaine and the vasoconstrictor nathalzoline.

The concentration or amount of vasoconstrictor to active agent in a formulation or mixture is a function of the particular active ingredient and the vasoconstrictor. More specifically, the ease with which the active agent can be delivered by iontophoresis is related to the characteristics of the vasoconstrictor, the active agent, and to some extent the iontophoretic system.

Iontophoretic administration rates are readily measured by protocols such as those disclosed in J. E. Riviere et al., *J. Toxicol—Cut. & Ocular Toxicol* 8:493 (1990). A range of useful concentrations of the vasoconstrictor with respect to the active agent is determined by analyzing the amount of active agent iontophoresed.

The concentration of the vasoconstrictor will effect enhanced skin concentrations of an active agent in two ways. When there is too much vasoconstrictor, it is believed there is a change of blood flow at the deeper blood vessels of the skin, thus closing shunt blood vessels which will divert blood flow from the upper capillary loops, and therefore prevent of active agent delivery and enhance skin concentration, thus reducing systemic active agent delivery. The other effect is the result of the introduction of additional ions that compete with the ions of the active ingredient during coiontophoresis. The present invention provides a method for determining the optimimum concentration of vasoconstrictor and active agent, which method accounts for competing ions in an iontophoretic system.

The present invention provides a method for obtaining optimum concentration at which enhancement of skin concentration of iontophoretic delivered active agents is maximized. Iontophoresis of a composition of vasoconstrictor and active agent is more efficient than iontophoresing active agent without a vasoconstrictor. The addition of vasoconstrictor permits the same delivery with a lower power. The method and composition for enhanced skin concentration of iontophoretic delivered active agents is especially beneficial for local skin effects such as when cutaneous anesthesia is desired.

The term "active agent" can more narrowly refer to a biologically active compound or mixture of compounds that have a therapeutic, prophylactic pharmacological, physiological, or combinations thereof, effect on the recipient and is sufficiently potent such that it can be delivered through the skin or other membrane to the recipient in sufficient quantities to produce the desired result.

The active agent for use in the method of the invention can be delivered alone, as a prodrug, or in combination with other substances. Other substances can include other permeation enhancers, buffers, bacteriostatics, stabilizers, antioxidants, other active agents and the like. In general, active agents include anesthetics, antiarthritics, antivirals, antineoplastics, antipruritics, antiinflammatories, muscle relaxants, antihistamines, antibiotics, and corticosteroids. Preferably the active agent is for non-systemic delivery. Specific examples of antibiotics include clindamycin, spectromycin and vancomycin. Specific examples of suitable corticosteroids include hydrocortisone and dexamethasone. Examples of antiarthritics include indomethacine and diclofenac. Antipruritics include dyclodine hydrochloride and benzocaine. A suitable antiviral includes acyclovir. Local anesthetics suitable for use include lidocaine, ropivicaine and mepivicaine. Preferably the active agent is a local anesthetic.

Primary requirements of an active agent are that it be charged or capable of modification to carry a charge. Appropriate selection of active agents for iontophoretic applications include a selection based on specific conductivity (i.e., estimates how easily drugs move in solution when an electric current is applied).

Active agent modification for iontophoretic delivery is guided by well-known procedures. For example, to deliver a positively charged drug, the chloride or hydrochloride form of the drug can be made and placed in the iontophoretic device reservoir for delivery. General texts in the field include *Remington's Pharmaceutical Sciences*, Ed. Arthur Osol, 16th ed., 1980, Mack Publishing Co., Easton, Pa. Typically the basic ($OH^-$ or amine) or acid ($H^+$) form of the active agent is made, depending on whether the anionic (negative charged ion) or cationic (positive charged ion) form of the active agent is to be delivered. Common modifications of active agents include modification to a halide salt form. For example, to deliver a positively charged active agent, the chloride or hydrochloride form of the active agent is made and placed in the iontophoretic device reservoir for delivery. Likewise, the composition is typically dissolved in a suitable solvent to obtain the ionic form for iontophoretic delivery. Suitable solvents include polar liquids such as water, glycerine, and lower alkyl alcohols such as methyl alcohol, ethyl alcohol, and branched alcohols such as isopropyl alcohol.

In this invention the effective amount of active agent means that amount needed to produce the intended result following its iontophoretic administration. The effective amount will vary, depending, among other factors, on the physiological effect as determined by the serum level of desired active agent, rate of clearance of active agent, and intradermal metabolism desired.

The term pharmaceutically acceptable composition refers to the addition salts, mild complexes, solid and liquid carriers, ionic forms, and the like, which do not significantly or adversely affect the properties of the active agent or its ability to be iontophoretically delivered. Pharmaceutically acceptable compositions can be prepared by reference to general texts in the field, such as *Remington's Pharmaceutical Sciences*, Ed. Arthur Osol, 16th ed., 1980, Mack Publishing Co., Easton, Pa.

Enhanced skin concentration and skin concentration enhancing amount refers to an amount which enhances the local skin concentration of active agent as compared to active agent delivered alone, but which amount does not present serious side effects which outweigh the advantages of its use.

The reservoir or similar structure that contains the active agent to be delivered can be in the form of any material suitable for making contact between the iontophoresis unit and the skin. Suitable materials include, but are not limited to, foams, ion exchange resins, gels and matrices.

Iontophoresis gels can be karaya gum, other polysaccharide gels, or similar hydrophilic aqueous gels capable of carrying ions. Specific examples of such gels include polyvinyl alcohol, polymethyl pyrollidine, methyl cellulose, polyacrylamide, polyhemas, polyhema derivatives and the like. The matrix selected should have nonirritating properties to avoid irritating the person's skin or tissue, suitable viscosity and surfactant properties to obtain good electrical contact with the skin or tissue, and the ability to act as a carrier medium for the ions.

Suitable vasoconstrictors include but are not limited to vasoconstrictors referred to as α-adrenergic agonist. Such vasoconstrictors include adrafinil, adrenolone, amidephrine, apraclonidine, budralazine, clonidine, cyclopentamine, detomidine, dimetofrine, dipivefrin, ephedrine, epinephrine, fenoxazoline, guanabenz, guanfacine, hydroxyamphetamine, ibopamine, indanazoline, isometheptene, mephentermine, metaraminol, methoxamine hydrochloride, methylhexaneamine, metizoline, midodrine, naphazoline, norepinephrine, norfenefrine, octodrine, octopamine, oxymetazoline, phenylephrine hydrochloride, phenylpropanolamine hydrochloride, phenylpropylmethylamine, pholedrine, propylhexedrine, pseudoephedrine, rilmenidine, synephrine, tetrahydrozoline, tiamenidine, tramazoline, tuaminoheptane, tymazoline, tyramine, and xylometazoline.

Although epinephrine is included as a vasoconstrictor, its use in the present invention is excluded, especially due to the fact it is rapidly degraded in the presence of oxygen and therefore is extremely difficult to work with. A preferred class of vasoconstrictors are imidazolines. Imidazolines include naphazoline (2-(1 naphthylmethyl) imidazoline), oxymetazoline (2-(4-tert-butyl-2, 6-dimethyl -3-hydroxbenzyl)-2-imidazoline), tetrahydrozaline (2-(1, 2, 3, 4-tetrahydro-1-naphthyl)-2-imidazoline)), fenoxazoline (2-[(o-cumenyloxy)methyl]-2-imidazoline), indanazoline (N-(2-imidazolin-2-yl)-N-(4-indanyl)amine), tramazoline (2-[(5, 6, 7, 8 tetrahydro-1-naphthyl)amino]-2-imidazoline, tymazoline (2-[(thymyloxy)-methyl]-2-imidazoline), and xylometazoline (2-(4-tert-butyl-2, 6-dimethylbenzyl)-2-imidazoline).

The treatment regimen for use in the present invention includes the consideration of a variety of factors, including the type, age, weight, sex, medical condition of the patient, severity of the condition and active agent to be delivered. An ordinarily skilled physician can readily determine and prescribe and administer the effective amount of the agent required to prevent or arrest the progress of the condition. In so proceeding, the physician could employ relatively low doses at first and subsequently increase the dose until a maximum response is obtained. Likewise, the decision of where to apply the iontophoretic system is a factor, depending on the area of application, for example, whether the area is on the torso or the extremities and whether those areas are hairy, wrinkled, folded or creased.

The following examples illustrate the specific embodiments of the invention described herein. As would be apparent to skilled artisans, various changes and modifications are possible and are contemplated within the scope of the invention described.

EXAMPLES

Material Preparation

Figure 2:
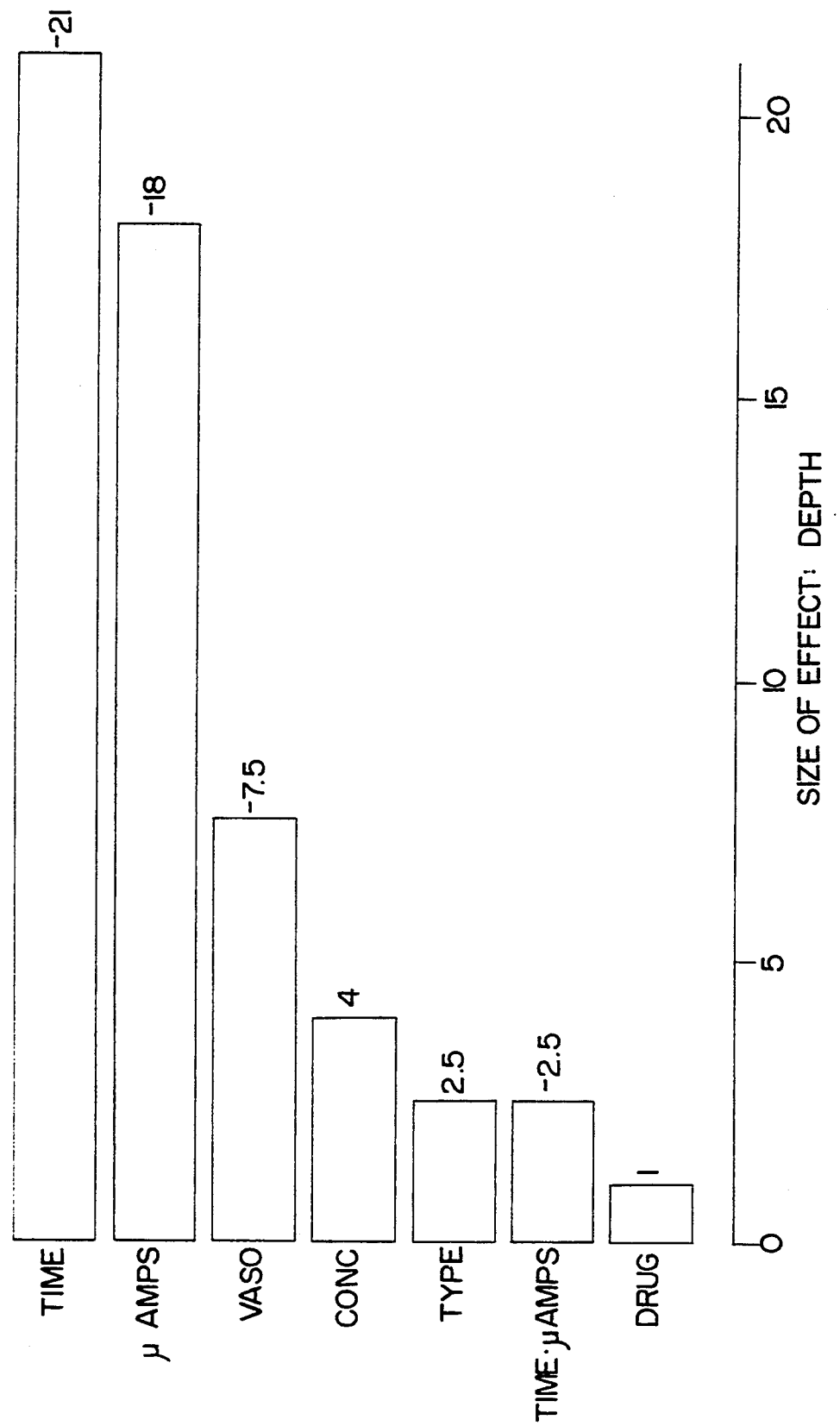
FIG. 2 Pareto chart of fractional factorial demonstrating the ability of a vasoconstrictor to enhance the depth of penetration of an active agent (Depth).
Figure 3:
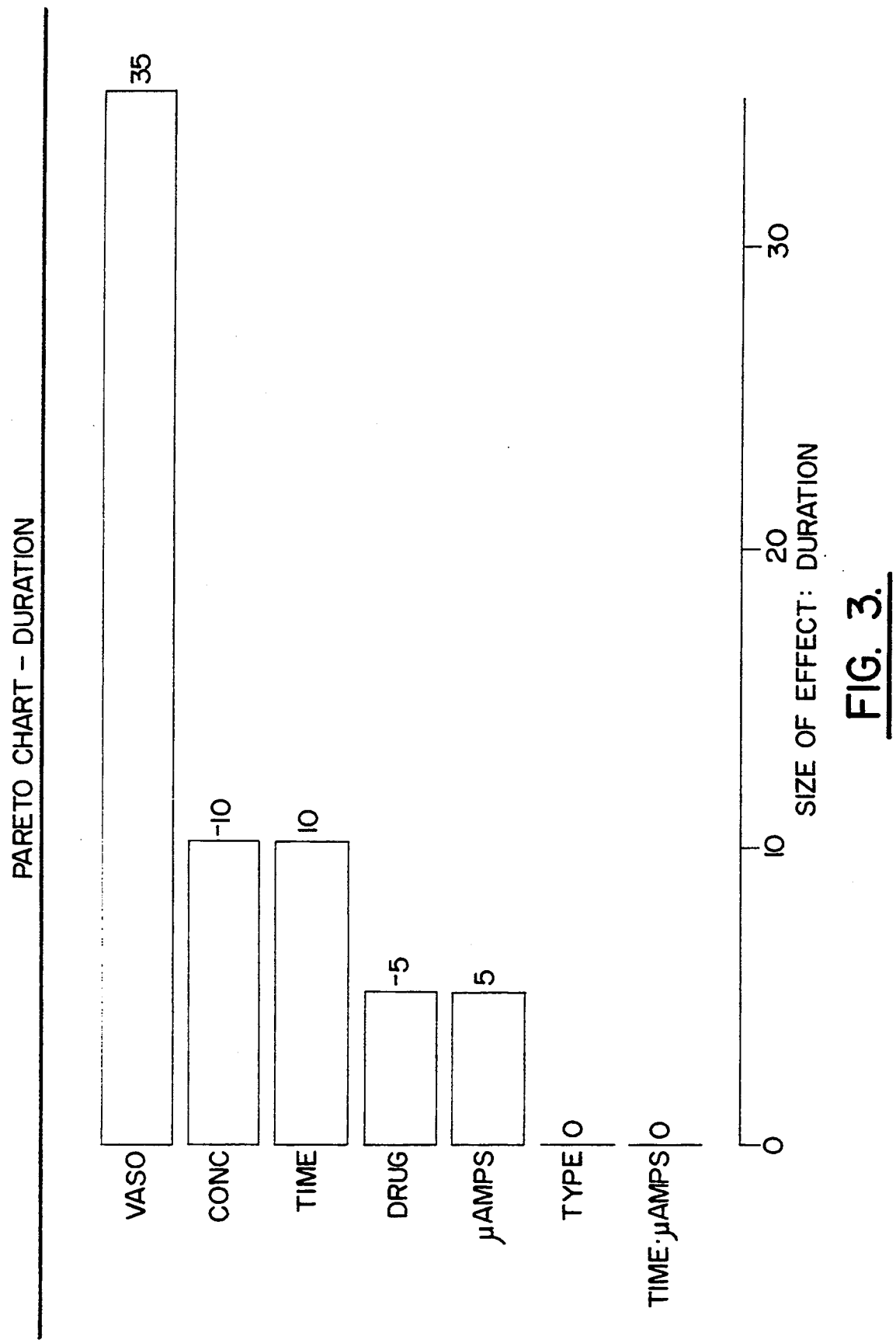
FIG. 3 Pareto chart of fractional factorial demonstrating the ability of a vasoconstrictor to enhance duration of an active agent's effect (Duration).
Figure 4:
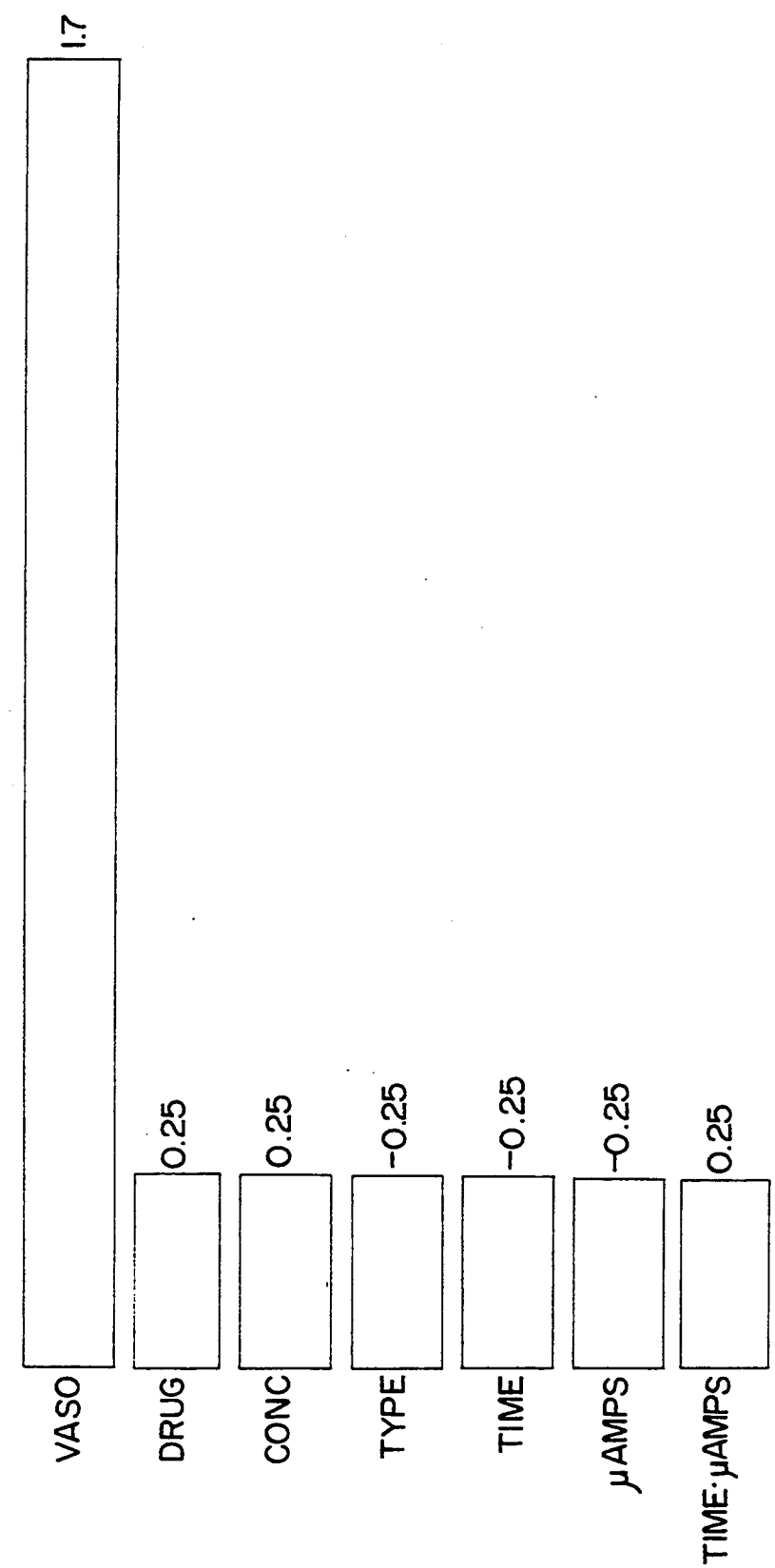
FIG. 4 Pareto chart of fractional factorial demonstrating enhanced blanching when a vasoconstrictor and active agent are iontophoresed.

The electrodes used herein have a surface area about 10 $cm^2$ (2.5 cm × 4 cm) and are fabricated as a sandwich. The outer layers of the sandwich consist of about 1/16 inch POREX TM (a thick porous, hydrophilic open-cell polyethylene foam into which a surfactant has been incorporated during manufacture, obtainable from Porex Technologies, Fairburn, Ga.). The inner layer of the sandwich electrode consists of about 1.5 cm×5 cm mesh of silver wire (0.0045 inch silver wire 80×80 weave, obtainable from Unique Wire Weaving Co., Pareto charts are prepared from the regression analysis. These charts are shown in FIGS. 2-4 for each response variable (i.e. depth, duration and blanching).

| Factors | A | B | C | D | E | F |
|---|---|---|---|---|---|---|
| Factor Names | time | uamps | drug | conc | vaso* | type |
| low (−1) | 4 | 200 | 1 | 0.04 | 0 | 2 |
| high (+1) | 10 | 500 | 2 | 0.15 | 1 | 4 |
| Response Variables | 1 depth | 2 duration | | 3 blanch | | |

| run | time | uamps | drug | conc | vaso* | type | depth | duration | blanch |
|---|---|---|---|---|---|---|---|---|---|
| 1 | 10 | 500 | 2 | 0.15 | 1 | 4 | 37 | 60 | 2 |
| 2 | 10 | 500 | 1 | 0.04 | 0 | 2 | 3 | 60 | 2 |
| 3 | 4 | 200 | 1 | 0.04 | 1 | 4 | 33 | 20 | 0 |
| 4 | 4 | 200 | 2 | 0.15 | 0 | 2 | 7 | 60 | 2 |
| 5 | 10 | 200 | 1 | 0.15 | 1 | 2 | 3 | 40 | 0 |
| 6 | 4 | 500 | 1 | 0.15 | 0 | 4 | 47 | 10 | 1 |
| 7 | 10 | 200 | 2 | 0.04 | 0 | 4 | 20 | 60 | 2 |
| 8 | 4 | 500 | 2 | 0.04 | 1 | 2 | 27 | 30 | 0 |

*vasoconstrictor

Hillside, N.J.). About 1.5 cm×1 cm tab of silver mesh is left protruding from the polyethylene sandwich for purposes of making electrical contact. The sandwich is held together by an epoxy type glue (e.g., DEVCON TM 5-minute epoxy glue, obtainable from Devcon Corp., St. Louis, Mo.) along the lateral edges of the polyethylene.

Using scissors, two rectangular pieces are cut from the 1/16 inch-thick sheet of POREX TM material. Each piece is about 2.5 cm×4 cm. A 1 cm×5 cm piece of the silver wire mesh is then cut. The mesh is longitudinally centered on one piece of the POREX TM, with about 1 cm of material extending out one end. A line of epoxy type glue is placed along the inner border of lateral edges and the end of the POREX TM. Take care not to place the glue on the wire mesh itself. It is both understood and desirable that the applied glue will contact the edges of the wire mesh and, by so doing, hold the mesh securely in position. However, the amount of that contact should be kept at a minimum.

Sandwich the wire mesh by placing the second piece of POREX TM over the first. Place the completed unit in the clamp and allow to dry about 40 minutes. Examine the electrode to see that all three glued edges are in tight contact. Test the integrity of the mesh-Porex TM attachment by gently tugging on the protruding edge of mesh. The mesh should not shift in position. Store in a dry area.

EXAMPLE 1

The Data collected during Fractional Factorial experiments (see B. Akerman et al., Acta pharmacol. Toxicol 45:58 (1978)), conducted according to the design below using lidocaine (Drug 1) and mepivocaine (Drug 2) with the vasoconstrictor naphazoline are analyzed using a multiple regression analysis available on STATGRAPHICS (STSC, Inc., Rockville, Md.). Values entered into the worksheet for the response variables are obtained as follows:
  depth: minimum percent response for experiment (average for the 6 animals)
  duration: time for response to return to 90% (or higher)
  blanch: no blanching observed during experiment=0 blanching observed occasionally during experiment=1 blanching observed across all animals for entire experiment=2

FIG. 2 shows that current time, and the presence of a vasoconstrictor have the most affect on depth; the "negative" effect of these three factors means that with increasing values for these factors, the value for depth decreases (i.e. the lower the percent response the better).

FIG. 3 shows that the presence of vasoconstrictor is the most significant effect on duration. The "positive" effect indicates when vasoconstrictors are present, the duration is longer. Concentration and time also played a significant role. Concentration, however, shows a negative effect on duration, meaning that with increased concentration the duration is for a shorter time. Active agent, type of electrode, uamps, and the time-current interaction appear to have an insignificant effect on duration.

FIG. 4 shows the effects on blanching. The only factor with a significant effect is the presence of vasoconstrictors.

EXAMPLE 2

Figure 5:
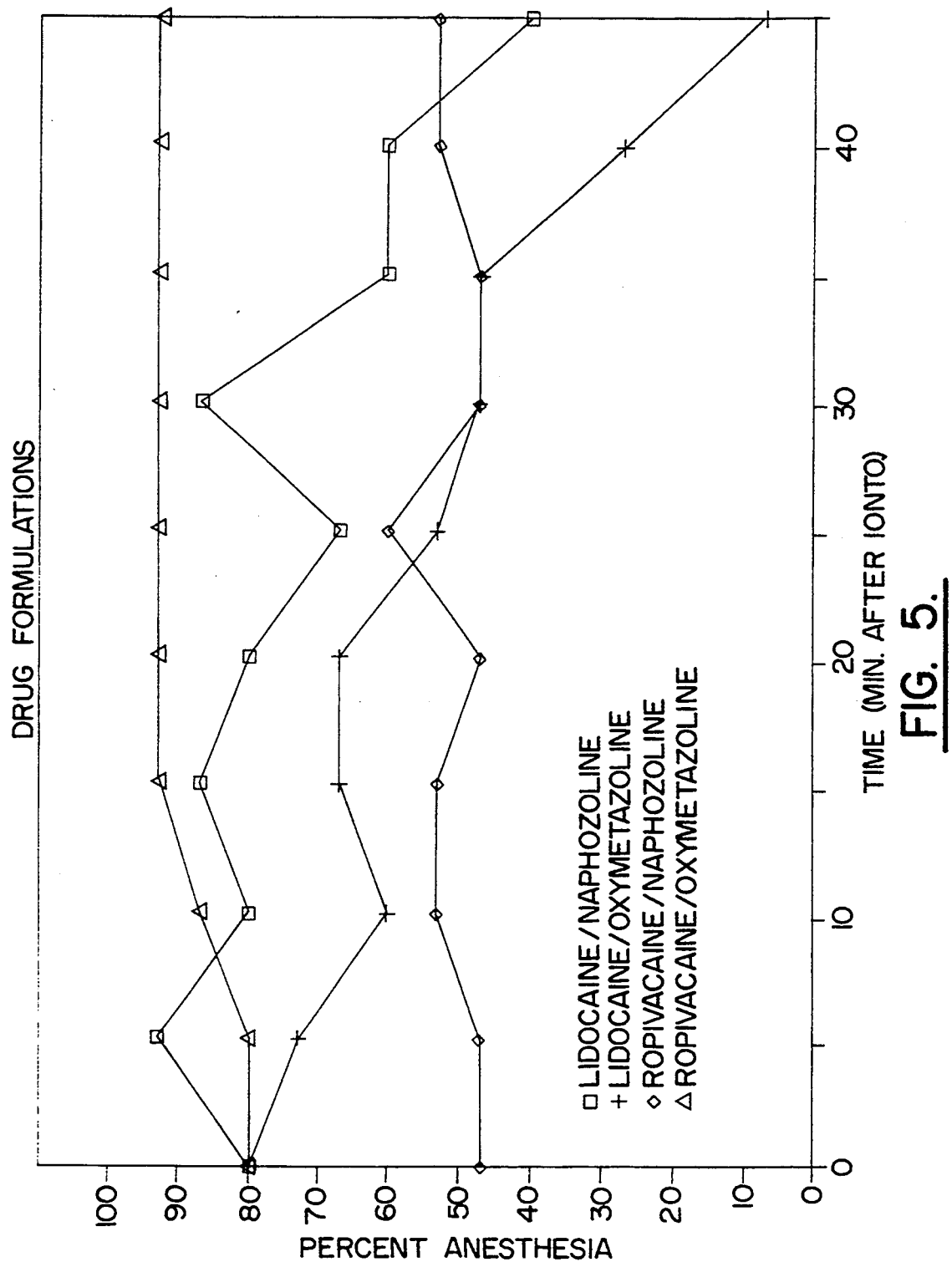
FIG. 5 Graph showing duration of anesthesia of active agents iontophoresed with vasoconstrictors.

Following procedures in substantial accordance with the teachings of Example 1, the combinations of lidocaine plus naphazoline, lidocaine plus oxymetazoline, ripivacaine plus naphazoline, and ripivacaine plus oxymetazoline were iontophoresed. As shown in FIG. 5, substantial duration of anesthetia is obtained when a vasoconstrictor is present with an active agent.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A method for enhancing skin concentration of iontophoretic delivered active agents comprising:
  (a) adding to an active agent an imidazoline vasoconstrictor in an amount effective to enhance the skin concentration of the active agent when delivered iontophoretically; and
  (b) delivering a pharmaceutically acceptable composition of said active agent and vasoconstrictor by iontophoresis.

2. The method of claim 1 in which the active agent is selected from the group consisting of therapeutics, anesthetics, hormones and proteins.

3. The method of claim 2 in which the active agent is an anesthetic.

4. A method for enhancing skin concentration of iontophoretic delivered active agents comprising:
(a) adding to an active agent a vasoconstrictor in an amount effective to enhance the skin concentration of the active agent when delivered iontophoretically; and
(b) delivering a pharmaceutically acceptable composition of said active agent and vasoconstrictor by iontophoresis, wherein said vasoconstrictor is an imidazoline selected from the group consisting of naphazoline, oxymetazoline, tetrahydrozaline, fenoxazoline, indanazoline, tramazoline, tymazoline, and xylometazoline.

5. The method of claim 4 in which the imidazoline is naphazoline.

6. The method of claim 5 in which the active agent is selected from the group consisting of lidocaine, ripivacaine and mepivacaine.

7. The method of claim 6 in which the active agent is lidocaine.

8. The method of claim 6 in which the active agent is ripivacaine.

9. The method of claim 6 in which the active agent is mepivacaine.

10. The method of claim 4 in which the imidazoline is oxymetazoline.

11. The method of claim 10 in which the active agent is selected from the group consisting of lidocaine, ripivacaine, and mepivicaine.

12. The method of claim 11 in which the active agent is lidocaine.

13. The method of claim 11 in which the active agent is ripivocaine.

14. The method of claim 11 in which the active agent is mepivacaine.

* * * * *